United States Patent
Wei et al.

(10) Patent No.: US 12,290,341 B2
(45) Date of Patent: May 6, 2025

(54) METHODS FOR DETERMINING A BLOOD PRESSURE VALUE OF A PATIENT, BLOOD PRESSURE MONITORS AND DIALYSIS SYSTEMS

(71) Applicant: Fresenius Medical Care Deutschland GmbH, Bad Homburg (DE)

(72) Inventors: Zhang Wei, Niederwerrn (DE); Christof Rüth, Hammelburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 489 days.

(21) Appl. No.: 17/426,417

(22) PCT Filed: Jan. 29, 2020

(86) PCT No.: PCT/EP2020/052138
§ 371 (c)(1),
(2) Date: Jul. 28, 2021

(87) PCT Pub. No.: WO2020/157114
PCT Pub. Date: Aug. 6, 2020

(65) Prior Publication Data
US 2022/0095938 A1  Mar. 31, 2022

(30) Foreign Application Priority Data
Jan. 29, 2019 (DE) .......................... 102019102178.2

(51) Int. Cl.
*A61B 5/021* (2006.01)
*A61B 5/00* (2006.01)
(Continued)

(52) U.S. Cl.
CPC ...... *A61B 5/02116* (2013.01); *A61B 5/02125* (2013.01); *A61B 5/02416* (2013.01);
(Continued)

(58) Field of Classification Search
CPC ............ A61B 5/02116; A61B 5/02125; A61B 5/02416; A61B 5/0295; A61B 5/7278;
(Continued)

(56) References Cited

U.S. PATENT DOCUMENTS

2017/0188850 A1* 7/2017 Banet ...................... A61B 5/021
2019/0159739 A1* 5/2019 Shah .................... G08B 21/182

FOREIGN PATENT DOCUMENTS

EP  3427651  1/2019
GB  2552455  1/2018
(Continued)

OTHER PUBLICATIONS

Shin, H. et al. Feasibility study for the non-invasive blood pressure estimation based on ppg morphology: normotensive subject study, Jan. 2017, BioMedical Engineering OnLine, 16:10 (Year: 2017).*
(Continued)

*Primary Examiner* — Christopher L Cook
*Assistant Examiner* — Dean N Edun
(74) *Attorney, Agent, or Firm* — Fish & Richardson P.C.

(57) ABSTRACT

The present disclosure relates to a method for determining a blood pressure value of a patient. The method comprises a step of determining a pulse course of the patient; a step of determining a reference point in the pulse course within a transition area from systole to diastole of a cardiac cycle of the patient; and a step of determining the blood pressure value based on the determined reference point.

16 Claims, 6 Drawing Sheets

(51) Int. Cl.
*A61B 5/024* (2006.01)
*A61B 5/0295* (2006.01)
*A61M 1/16* (2006.01)
*G16H 40/67* (2018.01)
*G16H 50/30* (2018.01)

(52) U.S. Cl.
CPC .......... *A61B 5/0295* (2013.01); *A61B 5/7278* (2013.01); *A61M 1/1603* (2014.02); *G16H 40/67* (2018.01); *G16H 50/30* (2018.01); *A61M 2230/30* (2013.01)

(58) Field of Classification Search
CPC ... A61B 5/6816; A61B 5/6824; A61B 5/6826; A61B 5/6829; A61B 5/6831; A61B 5/7264; A61B 5/0261; A61B 5/7239; A61M 1/1603; A61M 2230/30; A61M 2205/3561; A61M 2205/3592; A61M 2230/04; A61M 1/14; G16H 40/67; G16H 50/30
See application file for complete search history.

(56) References Cited

FOREIGN PATENT DOCUMENTS

| WO | WO-2004034897 A1 * | 4/2004 | ......... A61B 5/14551 |
| WO | WO 2009/013287 | 1/2009 | |
| WO | WO 2015/092753 | 6/2015 | |

OTHER PUBLICATIONS

Gu. W et al. 2008, A Novel Parameter from PPG Dicrotic Notch for Estimation of Systolic Blood Pressure Using Pulse Transit Time. Proceedings of the 5th International Workshop on Wearable and Implantable Body Sensor Networks, Jun. 2008, 86-88 (Year: 2008).*
Fischer, C. et al. 2019, Continuous non-invasive determination of nocturnal blood pressure variation using photoplethysmographic pulse wave signals: comparison of pulse propagation time, pulse transit time and RR-interval. Physiological Measurement. 40. Jan. 10, 2019. 014001 (Year: 2019).*
International Search Report and Written Opinion in International Appln. No. PCT/EP2020/052138, mailed Apr. 14, 2020, 21 pages (with English translation).
Kachuee et al., "Cuffless Blood Pressure Estimation Algorithms for Continuous Health-Care Monitoring," IEEE Transactions on Biomedical Engineering, Apr. 2017, 64(4):859-869, 11 pages.
Qawqzeh et al., "Photoplethysmogram reflection index and aging," International Conference on Graphic and Image Processing (ICGIP 2011), Oct. 2011, 8285:82852R-1-82852R-6.
Yousef et al., "The Analysis of PPG Morphology: Investigating the Effects of Aging on Arterial Compliance," Measurement Science Review, Dec. 2012, 12(6):266-271.

* cited by examiner

METHODS FOR DETERMINING A BLOOD PRESSURE VALUE OF A PATIENT, BLOOD PRESSURE MONITORS AND DIALYSIS SYSTEMS

CROSS-REFERENCE TO RELATED APPLICATIONS

The present application is the national stage entry of International Patent Application No. PCT/EP2020/052138, filed on Jun. 29, 2020, and claims priority to Application No. 10 10 2019 102 178.2, filed in the Federal Republic of Germany on Jan. 29, 2019, the disclosures of which are expressly incorporated herein in their entireties by reference thereto.

TECHNICAL FIELD

The present disclosure relates to methods for determining a blood pressure value of a patient and to a corresponding blood pressure monitor. Further, the disclosure relates to dialysis systems comprising such a blood pressure monitor.

BACKGROUND

Dialysis devices are known for performing hemodialysis. In such devices, blood of a patient circulates through an extracorporeal circuit and thereby is guided through a dialyzer unit. By doing so, undesirable substances are removed from the blood, while a reduction of body water takes place.

During hemodialysis, substances and fluids are exchanged along a semipermeable membrane, also referred to as a dialyzer, due to diffusion by using concentration gradients between the patient's blood and a correspondingly designed and provided dialysate.

Furthermore, dialysis devices are known for performing hemofiltration. In such devices, substances and fluid volumes are removed from the patient's blood in an extracorporeal circuit by means of a semipermeable membrane of a dialyzer which is subjected to a pressure gradient. Salts and other substances are removed from the patient's blood upon passing the dialyzer because of the pore size of the membrane. In order to compensate for the increased removal of fluid volume, typically, a substitution fluid is added to the patient's blood after passing the dialyzer.

To that end, a combination of the two methods is known, which is referred to as hemodiafiltration. Accordingly, during the dialysis treatment, water, e.g., plasma water is extracted from the patient's body. However, this may affect the patient's cardiovascular system, i.e., by reducing blood volume.

During hemodialysis, intradialytic hypotension is considered as one of the most common complications which may lead to nausea, vomiting, headaches, dizziness, cramps, fatigue, skin pallor, cold sweat and/or unconsciousness of the patient and, accordingly, requires appropriate care and intervention. This may be caused by an excessive or too rapid removal of water from the patient's blood and/or a deficient supply of substitution fluid into the blood, which is also referred to as "refilling".

As an indicator for such an intradialytic hypotension, a decrease in systolic blood pressure and/or in diastolic blood pressure and/or a decrease in mean arterial blood pressure may be used.

In known dialysis devices, a cuff-based, non-invasive blood pressure monitor is used for measuring systolic blood pressure values by applying an oscillometric method. Typically, in such devices, systolic blood pressure values are obtained intermittently, e.g., hourly, during the medical treatment. In other words, in the known dialysis devices, a non-continuous method is used for monitoring the patient's blood pressure. However, since an acute drop in blood pressure can occur quickly, for example within 10 minutes, such a measuring method is not suitable to ensure early and reliable detection of intradialytic hypotension.

SUMMARY

Based on the known prior art, it is an aspect of the present invention to provide an improved method for determining a blood pressure value of a patient and a corresponding blood pressure monitor for use in a dialysis system, which enable a continuous and continuing monitoring of a patient's blood pressure value and can be implemented in a cost-efficient manner.

This aspect is provided by a method for determining a blood pressure value of a patient, a blood pressure monitor, and a dialysis system. Preferred embodiments are set forth in the present specification, the Figures as well as the dependent claims.

Accordingly, a method for determining a blood pressure value of a patient is provided, comprising a step of determining a pulse course of the patient; a step of determining a reference point in the pulse course within a transition area from systole to diastole of a cardiac cycle of the patient; and a step of determining the blood pressure value based on the determined reference point.

Since, in the proposed method, blood pressure values are determined on the basis of a pulse course, it is enabled to continuously monitor the patient's blood pressure level over a long period of time, for example during the entire treatment time of a dialysis treatment. To that end, compared to the oscillometric measurement methods used in known dialysis devices, which are carried out by means of a cuff-based blood pressure monitoring device, the proposed method may be performed with less effort.

Specifically, in the proposed method, determining the patient's blood pressure value on the basis of the pulse course is enabled by the reference point which is determined in the pulse course. It has been found that a correlation between the reference point and the patient's blood pressure value of a cardiac cycle is provided. In other words, the reference point correlates to an associated blood pressure value. In this way, blood pressure values may be reliably determined as a function of the reference point.

More specifically, according to the proposed method, a reference point is determined which indicates a transition area from systole to diastole of a cardiac cycle of the patient.

The terms "systole" and "diastole" refer to different phases or parts of the cardiac cycle of the patient. In this context, the term "systole" generally refers to the part of the cardiac cycle during which the heart muscle is contracted and blood is pumped from the ventricles to the circulatory system. To that end, the term "diastole" refers to the part of the cardiac cycle indicating a relaxation phase of the heart during which the ventricles refill with blood. The phase transition from systole to diastole in the cardiac cycle is also referred to as "incisura" which corresponds to the time during which the aortic valve closes.

In a pulse course or pulse curve, the time during which the aortic valve closes may be detected on the basis of hydrodynamic effects, e.g., due to the elasticity of vessel walls or due to the Windkessel effect, which cause a temporary increase in the pulse course. Based thereupon, the incisura of a healthy heart can be detected in an area between the systole and diastole of the cardiac cycle.

As set forth above, the reference point to be determined is disposed within the transition area of the pulse course which indicates a transition from systole to diastole of the cardiac cycle. In the context of the present disclosure, the term "transition area from systole to diastole" refers to an area or section of the pulse course during which the phase transition from systole to diastole of the patient's cardiac cycle takes place. Accordingly, the incisura of the cardiac cycle is disposed within the transition area.

By determining the reference point, as indicated by the designation of the term itself, a reference parameter is provided for characterizing or specifying the pulse course of the cardiac cycle. In this way, a comparison of pulse courses among different cardiac cycles is enabled. The reference point may be a point of the pulse course, e.g., within the transition area of the pulse course, which is mathematically definable.

By disposing the reference point within the transition area from systole to diastole of the cardiac cycle, it is ensured that the reference point, at least approximately, is orientated or linked to the incisura. In other words, from a time-related perspective, the reference point may fall within the range of the incisura or coincide with it.

In the proposed method, the transition area of the pulse course indicating the transition phase from systole to diastole of the patient's cardiac cycle may be disposed between a local minimum and a local maximum of the pulse course. For example, the transition area may extend from the local minimum to the local maximum of the pulse course.

For defining the transition area, the proposed method may further comprise a step of determining a local minimum and/or a local maximum in the pulse course. This step may be performed based on a rate of change or alteration rate of the pulse course. The rate of change or the alteration rate, in this context, corresponds to a first derivative of the pulse course. At the local minimum and local maximum, the pulse course has a rate of change or alteration rate that equals zero. Thus, by determining at which point the rate of change or alteration rate of the pulse course equals zero, a local minimum or local maximum of the pulse course may be determined.

The proposed method may be used to determine and monitor a patient's blood pressure during a dialysis treatment, e.g., during a hemodialysis treatment. Accordingly, the proposed method may be applied in or carried out by a dialysis device or dialysis system. However, the proposed method is not limited to this application. Rather, the proposed method may be used in any application, where determination of a patient's blood pressure value is to be performed or required.

More specifically, the method may be intended or used for determining a systolic blood pressure value as the blood pressure value to be determined. In general, the term "systolic blood pressure" refers to a maximum value of the blood pressure occurring during a cardiac cycle or during one heartbeat.

Alternatively or additionally, the proposed method may be intended or used for determining a mean arterial pressure value as the blood pressure value to be determined. In the context of the present disclosure, the term "mean arterial pressure" generally refers to a mean value of the blood pressure course over time, e.g., during a cardiac cycle.

Alternatively or additionally, the proposed method may be intended or used for determining a diastolic blood pressure value as the blood pressure value to be determined. In general, the term "diastolic blood pressure" refers to a minimum value of blood pressure occurring during a cardiac cycle, i.e., in between two heartbeats.

The blood pressure value to be determined may be an absolute value of the blood pressure. Alternatively, the blood pressure value to be determined may be a relative blood pressure value, e.g., with regard to a reference blood pressure value. In this way, a change of the blood pressure value, i.e., during a medical treatment, may be indicated. For example, the reference blood pressure value may correspond to a blood pressure value of a preceding cardiac cycle. More specifically, the reference blood pressure value may correspond to a blood pressure value at the beginning of a monitoring procedure or at the beginning of a medical treatment, e.g., of a dialysis treatment.

As set forth above, the proposed method comprises the step of determining the time-dependent pulse course of the patient. In general, the term "pulse" refers to the mechanical effects of pressure and volume fluctuations in the blood circulation system of a patient's body which are caused by the systolic blood outflow. Specifically, different mechanical effects may be seen in the frequency of pressure surges, their amplitude and their time-dependent course. In the context of the present disclosure, the term "pulse course", also referred to as "pulse profile" or "pulse curve", may refer to a time course of the amplitude of the pulse at a part of the patient's body, for example at a patient's arm.

The pulse course may be determined in such a way that it at least partially indicates or represents a cardiac cycle of the patient. Alternatively, the pulse course may be determined in such a way that it indicates or represents at least one cardiac cycle of the patient. For example, the pulse course may be determined in such a way that it indicates or represents a plurality of cardiac cycles, i.e., successive cardiac cycles. The pulse course may be determined continuously, i.e., without interruptions. Accordingly, the pulse course determined in the proposed method may indicate or represent a continuously monitored course of the pulse, i.e., its amplitude. Alternatively or additionally, the pulse course may be determined intermittently, e.g., during intermittent time periods.

In a further development, the pulse course may be determined based on time- and volume-based blood flow values in a tissue section of the patient. For doing so, a photoplethysmography method may be used. The term "photoplethysmography" generally refers to an optical measurement technique for determining a change in volume of an organ, a tissue section supplied with blood or a blood vessel of a patient which is induced by pressure surges occurring in the circulatory system. For doing so, typically, an emitter is used for emitting light having a red or infrared wavelength characteristic into living tissue, wherein the light absorption is measured by means of a detector. In this configuration, the detector, on the basis of altered light absorption in the living tissue, obtains a volume-based measurement value. Generally, the degree of absorption of a living tissue increases with systole and decreased with diastole. In this way, the measurement of light absorption enables to determine the blood volume pulse.

More specifically, light absorption may be measured by means of a photoplethysmographic sensor, e.g., by means of a pulse oximeter. In this context, a distinction can be made between sensors which determine light absorption on the basis of light transmitted through living tissue and, on the other hand, sensors which determine light absorption on the basis of light reflected from the living tissue. For doing so, the sensor may be fastened to a part of the patient's body that is well supplied with blood, i.e., a forearm, a finger, a toe or an earlobe of the patient.

In a further development, the pulse course may be normalized. For doing so, the method may comprise a further step of normalizing the determined or measured pulse course. This may improve accuracy of determining the blood pressure value.

For example, the determined or measured pulse course may be normalized using an amplitude level, e.g., a maximal amplitude within a cardiac cycle, as a measure of scale. Accordingly, the pulse course may be an amplitude-normalized pulse course. In this way, the pulse course's susceptibility to amplitude fluctuations may be decreased.

Alternatively or additionally, the pulse course may be normalized using time as a measure of scale. Accordingly, the pulse course may be a time-normalized pulse course. For example, the pulse course may be normalized using the duration of one cardiac cycle. By normalizing the pulse course using the cardiac cycle duration as a measure of scale, the step of determining the blood pressure value may be less affected by heart rate variations.

A set forth above, the reference point may be a point of the pulse course which is mathematically definable, i.e., unambiguously definable. For determining the reference point, a rate of change or alteration rate of the pulse course may be taken into consideration. In other words, the reference point may be determined as a function of the rate of change or alteration rate of the pulse course. For example, the reference point may be determined on the basis of the above described local minimum or local maximum of the pulse course. The local minimum and the local maximum are unambiguously definable by means of the rate of change or alteration rate of the pulse course.

Alternatively or additionally, the reference point may be determined on the basis of a derivative of the rate of change of the pulse course. In this context, the derivative of the rate of change corresponds to the second derivative of the pulse course.

In a further development, the reference point may be determined on the basis of a point of inflection in the pulse course. For example, the reference point may correspond to the point of inflection in the pulse course. In general, the term "point of inflection" refers to a point on a continuous curve at which the curve changes from being concave to convex, or vice versa. For obtaining the point of inflection, a point of the pulse course may be determined, at which the value of the second derivative of the pulse course equals to zero, wherein the value of the third derivative of the pulse course at this point must be unequal to zero. The point of inflection that corresponds to the reference point may have a positive rate of change or slope. In this way, it may be ensured that the reference point is disposed within the transition area extending between the local maximum and local minimum.

In the following, the step of determining the blood pressure value on the basis of the reference point is further specified.

In a further development of the method, the step of determining a blood pressure value may be performed on the basis of a point in time and/or amplitude of the reference point. For example, the blood pressure value may be determined as a function of the point in time and/or the amplitude of the reference point, e.g., as a function of a quotient or ratio formed by the point in time and/or the amplitude of the reference point. The point in time of the reference point may be in the region of a systolic and/or diastolic duration or phase of the cardiac cycle.

In the step of determining the blood pressure value, a mathematical model or a mathematical function may be used. Accordingly, the proposed method may further comprise a step of providing the mathematical model or the mathematical function.

The mathematical model or function may be provided such that the blood pressure value as an output value is determined on the basis of at least one input variable, wherein the at least one input variable comprises the point in time and/or the amplitude of the reference point. Accordingly, the blood pressure value may be expressed as a function of the point in time and the amplitude of the reference point according to at least one of the following equations:

$$BP_n = F_1(t_{RP\_n}), \quad (1)$$

$$BP_n = F_2(h_{RP\_n}), \quad (2)$$

$$BP_n = F_3(t_{RP\_n}, h_{RP\_n}), \quad (3)$$

wherein $BP_n$ refers to the blood pressure value associated to the cardiac cycle n; F refers to a mathematical model or function; $t_{RP\_n}$ refers to the point in time of the reference point RP associated to the cardiac cycle n; and $h_{RP\_n}$ refers to the amplitude level of the reference point RP associated to the cardiac cycle n.

As set forth above, the step of determining the blood pressure value may be performed on the basis of a quotient or ratio formed by the point in time and the amplitude of the reference point. Accordingly, the blood pressure value may be expressed as a function of a quotient or ratio formed by the point in time and the amplitude of the reference point according to the following equation:

$$BP_n = F\left(\frac{t_{RP\_n}}{h_{RP\_n}}\right) \quad (4)$$

Specifically, the mathematical function may be a linear function. Accordingly, the above equations (1), (2) and (4) may be expressed as follows:

$$BP_n = c_1 + m_1 \times t_{RP\_n}, \quad (5)$$

$$BP_n = c_2 + m_2 \times h_{RP\_n}, \quad (6)$$

$$BP_n = c_3 + m_3 \times \frac{t_{RP\_n}}{h_{RP\_n}}, \quad (7)$$

wherein c refer to intercept constants of the linear functions; and m refer to slopes of the linear functions.

Alternatively, the mathematical function may be a polynomial function, e.g., a polynomial of degree two or of a higher degree.

The step of providing the mathematical function may be defined such that the mathematical function or model is derived or adapted based on measured values of the blood pressure and associated pulse courses. In this context, the adaption of a mathematical function or model may also be referred to as calibration.

More specifically, the step of providing the mathematical function may comprise a sub step of providing at least two data sets. Each data set may comprise a measured value of the blood pressure and an associated point in time and/or amplitude of the reference point. For example, the measured value of the blood pressure may be obtained by means of a cuff-based, non-invasive blood pressure monitor by applying an oscillometric measurement method. The thus measured values for the blood pressure may then be assigned to at least one determined reference point. The corresponding reference point may be determined based on a pulse course which, from a time-perspective point of view, is coupled to the measurement of the blood pressure value. Accordingly, the measured blood pressure value and the associated reference point may form a data set as described above.

In a further sub step, the mathematical function may then be determined or derived on the basis of the provided data sets. Specifically, the mathematical function may be determined or derived by applying an interpolation method or a regression analysis method, e.g., a linear regression analysis method, or by applying any other method for determining a polynomial function based on the associated data sets. Such methods for determining or deriving of mathematical functions on the basis of associated data sets are well known to a person skilled in the art and are thus not further specified.

In a further development, the method may further comprise a step of outputting a warning signal. In this step, the warning signal may be output when the determined blood pressure value has reached a predetermined threshold value. The predetermined threshold value may be defined with respect to a blood pressure value associated to a preceding cardiac cycle, e.g., at the beginning of a medical treatment, e.g., of a dialysis treatment.

When the blood pressure value to be determined corresponds to a systolic blood pressure value, the threshold value may be defined by subtracting a blood pressure value associated to a preceding cardiac cycle with a value of substantially 15 or 20 mmHg.

When the blood pressure value to be determined corresponds to a diastolic blood pressure value, the threshold value may be defined by subtracting a blood pressure value associated to a preceding cardiac cycle with a value of substantially 15 or 20 mmHg.

When the blood pressure value to be determined corresponds to a mean arterial pressure value, the threshold value may be defined by subtracting the blood pressure value associated to a preceding cardiac cycle with a value of substantially 7.5 or 10 mmHg.

Furthermore, a blood pressure monitor is proposed for determining a blood pressure value of the patient. The blood pressure monitor may be configured or intended for performing the above described method. Accordingly, technical features which are described in connection with the above method may also relate and be applied to the blood pressure monitor, and vice versa. Thus, these technical features are to be considered as disclosed for the blood pressure monitor as well.

The blood pressure monitor comprises a measuring unit for determining a pulse course of the patient. Further, the blood pressure monitor comprises a control unit for determining a reference point in the pulse course within a transition area from systole to diastole of a cardiac cycle of the patient. The control unit is further configured for determining the blood pressure value on the basis of the determined reference point.

The blood pressure monitor may be intended or used for determining or measuring blood pressure values during a dialysis treatment. However, the blood pressure monitor is not limited to this application. Specifically, the blood pressure monitor may be comprised in a dialysis system and may communicate with a dialysis device. Accordingly, the blood pressure monitor may comprise an interface for communicating with a dialysis device or any other device for exchanging, i.e., bidirectionally exchanging, information, e.g., measured or determined values.

The basic structure and basic function of a dialysis device or system are well known to the person skilled in the art and are thus not further specified. Rather, characteristics of the blood pressure monitor are addressed in the following.

The measuring unit may be configured to determine the pulse course on the basis of time- and volume-based blood flow values acquired on a living tissue section of the patient, i.e., by applying photoplethysmography. Thus, the measuring unit may be a photoplethysmographic measuring unit, e.g., a pulse oximeter. Further, the measuring unit may be designed and intended to be detachably attached to a tissue section of the patient which is well supplied with blood. For example, the measuring unit may be designed to be attached or fixed to a forearm, a finger, a toe and/or an ear of the patient. Accordingly, the measuring unit may be equipped with a wristband, a finger clip, a toe clip and/or an ear clip.

The blood pressure monitor may be used for continuously monitoring a pulse course of the patient. Further, the blood pressure monitor may be configured to determine for each cardiac cycle recorded during the monitoring of the at least one blood pressure value. This may be performed on the basis of the reference point obtained by the control unit, wherein the reference point is determined for each cardiac cycle recorded during the monitoring. In this way, a continuous monitoring of the blood pressure value, i.e., during a medical treatment, may be ensured.

For determining the blood pressure value on the basis of the determined reference point, the blood pressure monitor may make use or apply a mathematical model or function. The mathematical model or function, based on the reference point forming an input variable, may output the blood pressure value as an output value. The mathematical model or function may be stored in a memory unit of the blood pressure monitor. In this configuration, the control unit may have access to the memory unit and to the mathematical model or function stored therein. In this way, the control unit may determine the blood pressure value based on the determined reference point by applying or making use of the mathematical model or function stored in the memory unit.

In a further development, the control unit may be configured to determine a mathematical function to be stored in the memory unit and/or to adapt a mathematical function stored in the memory unit. This may be performed on the basis of measurement data or data sets provided or transmitted to the control unit. Each one of the data sets may comprise a measured blood pressure value and an associated reference point, e.g., an associated point in time and/or an associated amplitude of the reference point. The data sets provided to the control unit may be patient-specific. In this way, patient-specific medical models or functions for determining blood pressure values may be provided. Preferably, the data sets are provided such that the measured blood pressure values are obtained at a predefined part of the patient's body, i.e., at the same part of the patient's body.

According to one configuration, the control unit of the blood pressure monitor, via the interface, may receive blood pressure values measured at the patient. Based on the measured blood pressure values, the control unit may be configured to assign to each measured blood pressure value a pulse course of a cardiac cycle and/or a reference point in the pulse course, respectively. In this way, the control unit may generate at least two data sets, i.e., in each of which a measured blood pressure value is assigned to a corresponding reference point. Based on the thus generated data sets, the control unit may be configured to determine the mathematical function, e.g., by applying an interpolation method and/or a regression analysis method, e.g., a linear regression analysis method.

Alternatively, existing or already generated data sets may be transmitted to the blood pressure monitor via the interface. For example, the data sets may be generated by a device connected to the blood pressure monitor, e.g., by the dialysis device. In this configuration, the blood pressure monitor may transmit the time-dependent pules course to the device via the interface. Further, the mathematical function may be transmitted to the blood pressure monitor and be stored in the memory unit. Accordingly, the mathematical function may be provided or derived by the device connected to the blood pressure monitor.

For obtaining the measured blood pressure values, the device connected to the blood pressure monitor, e.g., the dialysis device, may comprise a further blood pressure monitor. The further blood pressure monitor may, for example, be a cuff-based, non-invasive blood pressure monitor configured to oscillometrically measure blood pressure values at regular intervals, e.g., every 10 minutes.

In a further development, the blood pressure monitor may further comprise an alarm unit configured for outputting a warning signal when the blood pressure value determined by the control unit has reached a predetermined threshold value. The warning signal may be an optical signal and/or an acoustic signal, e.g., an alarm signal. Specifically, the predetermined threshold value may be determined with respect to a blood pressure value associated to a preceding cardiac cycle, e.g., at the beginning of a medical or dialysis treatment. In this way, the blood pressure monitor may, for example, indicate the occurrence of intradialytic hypotension during a dialysis treatment.

Accordingly, the proposed blood pressure monitor may be configured for diagnosing intradialytic hypotension. In response to the warning signal generated by the blood pressure monitor, the dialysis device may take measures for counteracting a further drop in the patient's blood pressure. For doing so, the dialysis device may interrupt an ultrafiltration treatment, thereby preventing the patient's blood from being subjected to further dehydration. Alternatively or additionally, the dialysis device may initiate or cause repositioning of the patient so as to be position the patient in a stable position, for example in the so-called Tendelenburg position. Alternatively or additionally, in response to the warning signal, medical staff may be informed and/or a blood pressure measurement may be initiated to validate the drop in blood pressure.

Furthermore, a dialysis system is proposed which is equipped with the above-described blood pressure monitor. Accordingly, technical features which are described in connection with the above blood pressure monitor may also relate and be applied to the dialysis system, and vice versa. The dialysis system may further comprises a dialysis device, e.g., for performing hemodialysis, hemofiltration or hemodiafiltration treatments.

BRIEF DESCRIPTION OF THE DRAWINGS

The present disclosure will be more readily appreciated by reference to the following detailed description when being considered in connection with the accompanying drawings in which.

DETAILED DESCRIPTION

In the Figures, like elements are denoted by identical reference numerals and repeated description thereof may be omitted in order to avoid redundancies.

Figure 1:
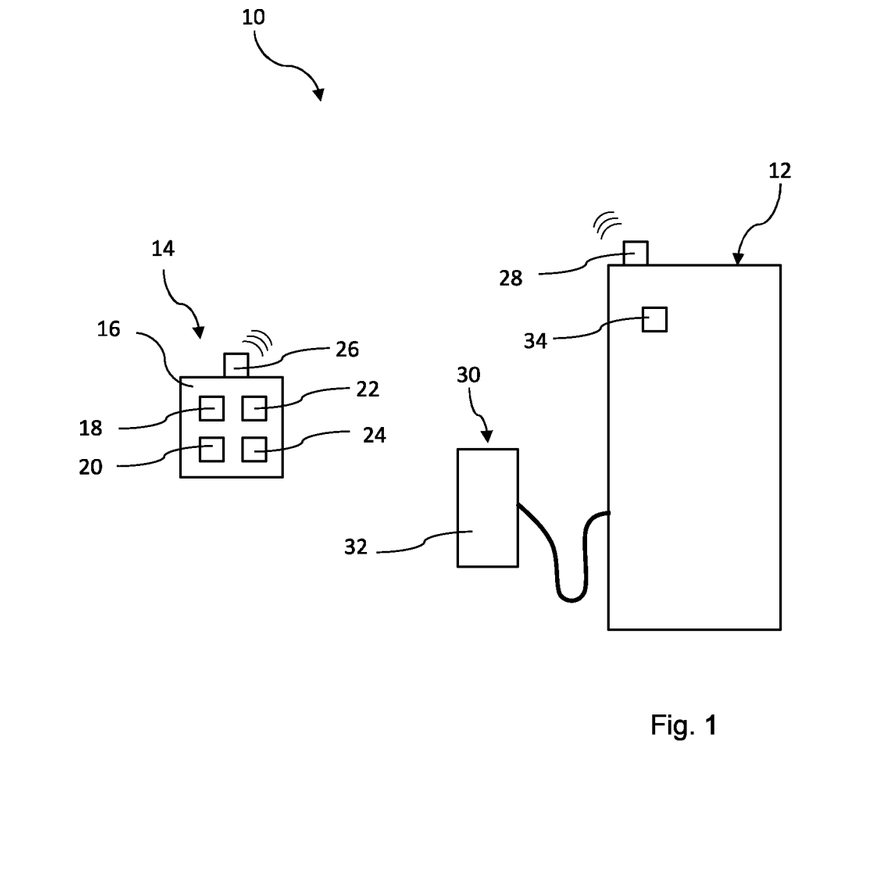
FIG. 1 is a schematic view of a dialysis system comprising a blood pressure monitor for determining a blood pressure value of a patient on the basis of a measured pulse course.

FIG. 1 schematically shows a dialysis system 10 configured for performing a hemodialysis treatment on a patient. The dialysis system 10 comprises a dialysis device 12 and a blood pressure monitor 14 for determining a blood pressure value of the patient on the basis of a measured pulse course or pulse profile.

The blood pressure monitor 14 comprises a wristband 16 configured for being detachably attached to a patient's forearm or upper arm during the dialysis treatment. The wristband 16 is equipped with a measuring unit 18, a control unit 20, a memory unit 22, an alarm unit 24 and a wireless interface 26. The wireless interface 26 is configured for exchanging data with a complementary designed wireless interface 28 provided at the dialysis device 12.

The measuring unit 18 is configured to measure or determine a time-dependent pulse course of the patient. Specifically, the measuring unit 18 is configured to measure the pulse course in a non-invasive manner. For example, the measuring unit 18 may be provided in the form of a photoplethysmographic measuring unit which uses photoplethysmography to measure time- and volume-based blood flow values on a tissue section of the patient, based on which it determines the patient's pulse course.

Figure 2:
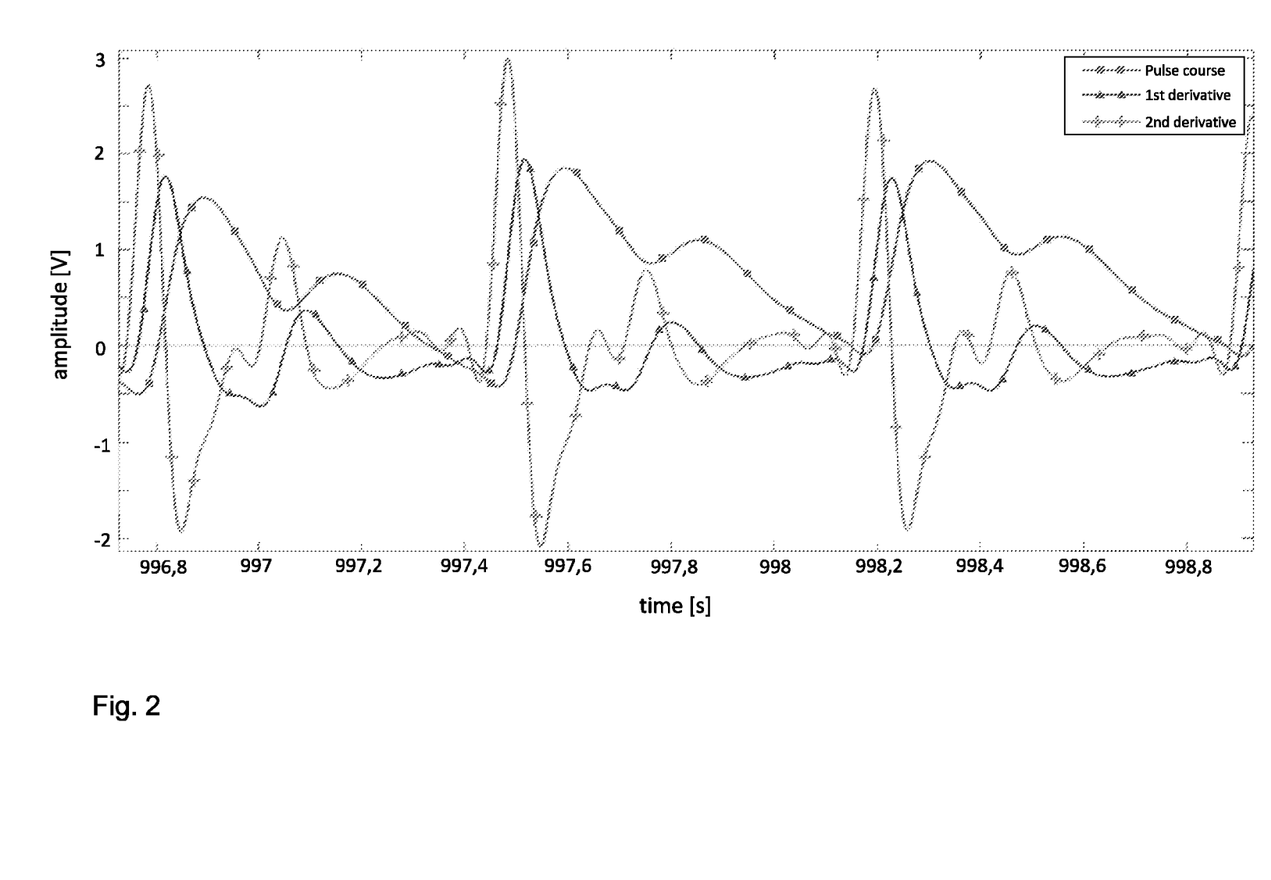
FIG. 2 shows a diagram illustrating a pulse course measured by the blood pressure monitor.

A pulse course of the patient determined by the measuring unit 18 is illustrated in the diagram depicted in FIG. 2. Specifically, the diagram depicted in FIG. 2 illustrates the course of amplitude level of the patient's pulse over a time range of three cardiac cycles. The abscissa of the diagram depicts the time and the ordinate depicts the associated amplitude level of a signal acquired by the measuring unit 18.

The control unit 20 is configured for processing the signal and data measured by the measuring unit 18. More specifically, the control unit 20 is configured to determine a reference point RP in the pulse course, wherein the reference point RP is disposed within a transition area TA of the pulse course indicating a transition phase from systole to diastole of a cardiac cycle of the patient. Further, the control unit 20 is configured to determine a blood pressure value of the patient based on the determined reference point.

Alternatively or additionally to the shown configuration, in which the photoplethysmographic measuring unit 18 is provided in the wristband 16, the photoplethysmographic measuring unit 18 may be provided in an ear clip, a finger clip or a toe clip.

Figure 3:
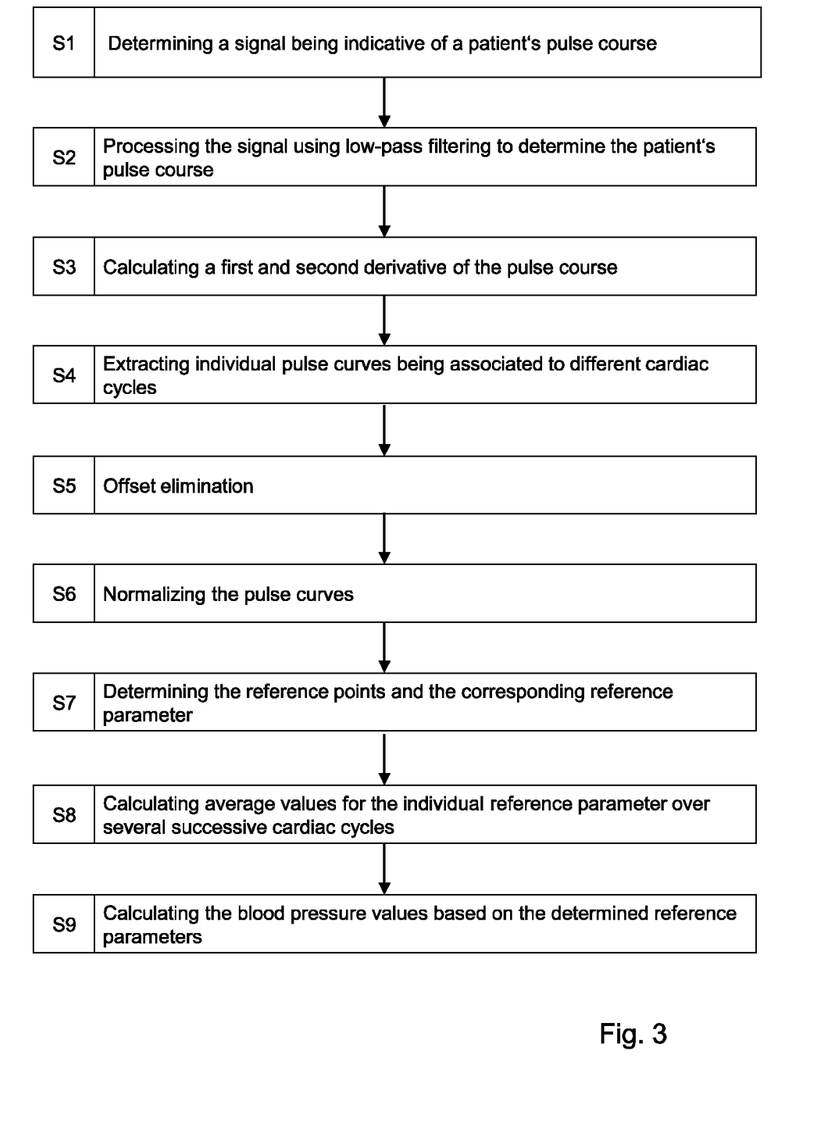
FIG. 3 shows a flow diagram illustrating a method performed by the blood pressure monitor for determining the blood pressure value of the patient.

In the following, a method performed by the control unit 20 for determining blood pressure values is specified.

In a first step S1 of the method, the measuring unit 18 detects or determines a signal being indicative of the pulse course of the patient which is transmitted to the control unit 20. In a second step S2, the control unit 20 performs low-pass filtering, e.g. for a frequency in the range of 20 Hz, in order to eliminate high-frequency distortions. As a result, the pulse course or pulse curve depicted in FIG. 2 is determined. Subsequently, in a third step S3, the control unit 20 calculates a first and a second derivative or derivation of the pulse course, which are depicted in FIG. 2 and which are used for determining the reference point RP.

In a further step S4, the control unit 20 is configured to determine individual cardiac cycles or individual pulse curves associated to different cardiac cycles in the pulse course and to extract them for further processing. For doing so, the control unit 20 may be configured to determine a starting point and an end point for each pulse curve.

The subsequent steps S5 to S7 are then performed for each one of the detected pulse curves or, in other words, for the pulse curve for each one of the detected cardiac cycles.

Figure 4:
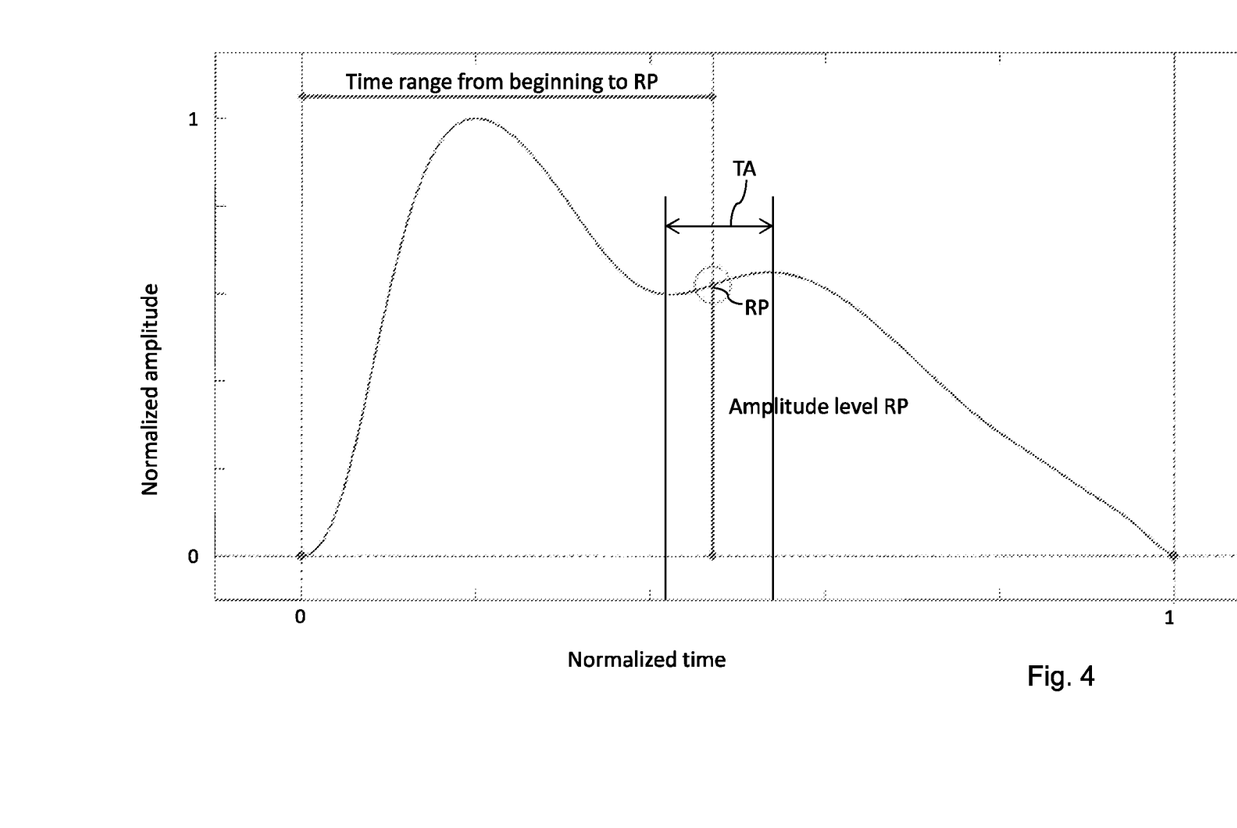
FIG. 4 shows a diagram illustrating a normalized pulse course of a patient's cardiac cycle.

In step S5, an offset elimination is performed for each one of the pulse curves before, in step S6, an amplitude-based and time-based normalization of the pulse curves is performed. For doing so, at first, a maximum amplitude and a cardiac cycle duration or cardiac period are determined for each one of the pulse curves. Then, the amplitude of each one of the pulse curves is normalized using the associated maximum amplitude as a measure of scale and the width of the pulse curve is normalized using the associated cardiac cycle duration as a measure of scale. In this way, a normalized pulse course is determined for each one of the cardiac cycle. Such a normalized pulse course is depicted in FIG. 4. Specifically, FIG. 4 shows a diagram illustrating a normalized pulse course for one cardiac cycle, wherein the abscissa shows normalized time duration values and the ordinate shows normalized amplitude values.

In a further development, patient-specific parameters may be determined. The patient-specific parameters may be transmitted to the control unit 20, for example, from a patient file or patient card which, e.g., may be obtained by the dialysis device 12 and may be transmitted to the control unit 20.

In the step S7, based on the normalized pulse course, a reference point RP is determined in the pulse course for each cardiac cycle. Specifically, the reference point RP refers to a mathematically definable point in the pulse course within a transition area TA being indicative of a transition phase from systole to diastole of the cardiac cycle. The transition area TA is depicted in FIG. 4 and extends between a local minimum and a local maximum of the pulse course. More specifically, the reference point RP corresponds to a point of inflection in the pulse course, at which the pulse curve has a positive rate of change or slope. For determining the point of inflection, the control unit 20 makes use of the determined second derivative of the pulse course. In other words, the control unit 20 determines the reference point RP on the basis of the second derivative of the pulse course. Specifically, for doing so, the control unit 20 may be configured to determine a point of the pulse course in an area between the local minimum and the local maximum, at which the second derivative of the pulse course equals to zero.

Then, based on the determined reference point RP, a point in time of the reference point RP, an amplitude level of the reference point RP and a quotient or ratio formed by the point in time and amplitude of the reference point RP are determined for each one of the identified cardiac cycles. Hereinafter, these parameters are referred to as reference parameters.

Thereafter, in a further step S8, an average value for each reference parameter is calculated for successive cardiac cycles. This may be performed continuously during the method. For example, the control unit 20 may be configured to calculate the average value for the reference parameters among the cardiac cycles on the basis of three successive cardiac cycles.

In the a step S9, the control unit 20 determines a systolic blood pressure value on the basis of at least one of the following three linear functions:

$$SBP = c_1 + m_1 \times \bar{t} \tag{8}$$

$$SBP = c_2 + m_2 \times \bar{h}, \tag{9}$$

$$SBP = c_3 + m_3 \times \frac{\bar{t}}{\bar{h}}, \tag{10}$$

wherein SBP refers to a systolic blood pressure value; c refers to an intercept constant of the linear functions; m refers to a slope of the linear functions; $\bar{t}$ refers to an average value of the point in time of the reference point over, for example, 2 to 20, i.e., 5 to 20, cardiac cycles; $\bar{h}$ refers to an average value of the amplitude level of the reference point over, for example, 2 to 20, i.e., 5 to 20, cardiac cycles.

Further, a moving average may be used, wherein a window size for each one of the considered parameters may be selected in dependence on a desired or required accuracy.

Alternatively, in step S9, the control unit 20 may determine a mean arterial blood pressure value on the basis of the determined reference parameters by means of a corresponding mathematical function.

The linear functions are preferably stored in a memory unit 22 of the blood pressure monitor 14. Alternatively, as regards the above described linear functions, at least one polynomial function, e.g., a polynomial of degree two or of a higher degree, may be used for determining the blood pressure values.

In the shown dialysis system 10, the dialysis device 12 is configured to derive the above described linear functions for determining the patient's blood pressure values and/or to adapt the linear functions during operation. Alternatively, the control unit 20 of the blood pressure monitor 14 may be configured to derive the above described linear functions for determining the patient's blood pressure values and/or to adapt the linear functions during operation. This may be performed on the basis of data sets provided by the dialysis device 12. Each of the data sets comprises a measured blood pressure value and an associated reference point, e.g., associated reference parameters.

In order to generate the measured blood pressure values, the dialysis device 12 comprises a further blood pressure monitor 30. Specifically, the further blood pressure monitor 30 is a cuff-based, non-invasive blood pressure monitor, which is configured to oscillometrically measure patient's blood pressure values at regular intervals during the dialysis treatment, for example every 10 minutes or hourly. For doing so, a cuff 32 of the blood pressure monitor 30 is fixed to an arm of the patient, via which a systolic and/or diastolic blood pressure value of the patient is measured.

The dialysis device 12 is configured to assign to each one of the measured blood pressure values a corresponding reference point and the corresponding reference parameter of the reference point. In this way, the data sets are generated. Specifically, the control unit 20 is configured to transmit to the dialysis device 12 the determined reference parameters which correspond to blood pressure values determined by means of the further blood pressure monitor 30. The thus generated data sets are stored in a further memory unit 34 in the dialysis device 12.

Figure 5:
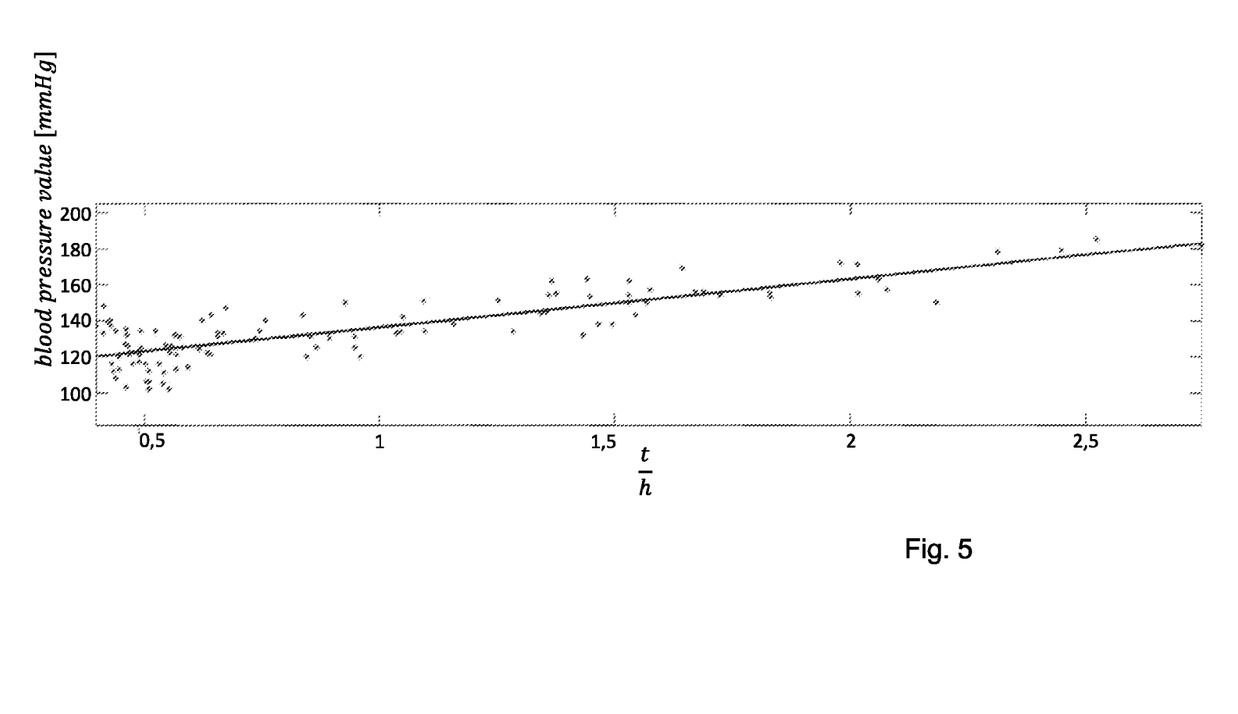
FIG. 5 shows a diagram illustrating a correlation between measured blood pressure values and determined reference points.

FIG. 5 shows a diagram illustrating data sets which are generated in such a way. Each one of the data sets comprises a measured blood pressure value and a corresponding reference quotient. In the diagram, the data sets are represented in the form of dots. The reference quotient refers to a ratio in which the point in time of a reference point is divided by its amplitude level. Accordingly, the abscissa of the diagram shows a value of the reference quotient and the ordinate quantifies the measured blood pressure value.

The dialysis device 12 is configured to determine the mathematical functions, i.e., the coefficients $c_{1-3}$ and $m_{1-3}$ of the above equations (8), (9) and (10), based on the data sets stored in the further memory unit 34 by applying a linear regression analysis method. With regards to equation (10), the result of this method step is illustrated in the diagram depicted in FIG. 5 in the form of a linear function.

Once the mathematical functions have been determined or adapted, the coefficients $c_{1-3}$ and $m_{1-3}$ of the above equations (8), (9) and (10) are transmitted to the blood pressure monitor 14 via the interfaces 26, 28 and stored in the memory unit 22. In this way, it can be ensured that the control unit 20 calculates the blood pressure values on the basis of the mathematical functions determined or adapted by the dialysis device 12.

The dialysis device 12 is configured to calibrate or adjust the mathematical functions, e.g., the coefficients $c_{1-3}$ and $m_{1-3}$, at regular and predefined intervals, for example every three or four weeks. Further, the dialysis device 12 is configured to transmit the determined coefficients $c_{1-3}$ and $m_{1-3}$ to the blood pressure monitor 14 before starting a dialysis treatment.

Figure 6:
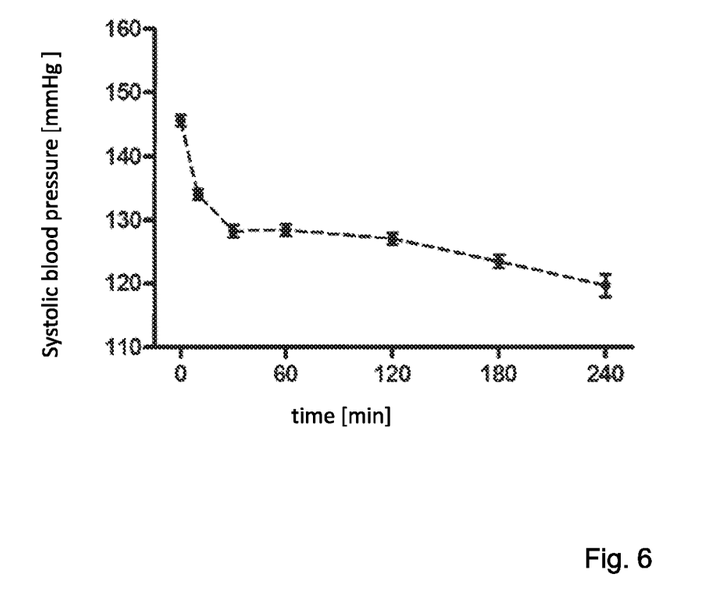
FIG. 6 shows a diagram illustrating an average course of a patient's systolic blood pressure during a hemodialysis treatment.

Alternatively or additionally, the step of determining and adjusting the mathematical functions as well as the step of transmitting the same to the blood pressure monitor 14 may be performed during the dialysis treatment. FIG. 6 depicts a diagram which illustrates an average course of the patient's systolic blood pressure during a hemodialysis treatment. The abscissa of the diagram shows the time and the ordinate shows the systolic blood pressure. As can be gathered from the diagram, the systolic blood pressure rapidly drops within the first 30 minutes of the dialysis treatment. Based on this finding, it may be advantageous to acquire data sets used for adapting or deriving the mathematical functions at the beginning of the dialysis treatment. These data sets then may be used to adapt or provide the mathematical functions, based on which, in the further course of the treatment, blood pressure values may be determined.

In an alternative configuration, the blood pressure monitor 14 and the further blood pressure monitor 30 may be accommodated in a single wristband or cuff. In this way, it may be ensured that both blood pressure monitors perform measurements at the same part of the patient's body. This may improve patient's comfort. Further, the blood pressure monitor 14 may be configured to determine a blood pressure value before and after a measurement performed by the further blood pressure monitor 30.

The blood pressure monitor 14 further comprises the alarm unit 24 configured for outputting a warning signal. The alarm unit 24 is configured to output the warning signal when the blood pressure value determined by the control unit 20 reaches or falls below a threshold value. More specifically, the alarm unit 24 is configured to output the warning signal when the control unit 20 determines that a blood pressure value determined by the control unit 20 during the dialysis treatment falls at least 15 or 20 mmHg below a blood pressure value determined or measured at the beginning of the dialysis treatment. In other words, in this configuration, the threshold value refers to an absolute value change of the determined blood pressure value with respect to a measurement of the blood pressure value at the beginning of the dialysis treatment. Alternatively, the threshold value may refer to a relative value change of the determined blood pressure value with respect to a measurement of the blood pressure value at the beginning of the dialysis treatment.

The alarm unit 24 is configured to generate an optical or acoustic alarm in response to the generated warning signal. Further, the alarm unit 24 is configured to transmit the generated warning signal to the dialysis device 12 via the interface 26. The dialysis device 12 may be configured to carry out a blood pressure measurement in response to the received warning signal by means of the further blood pressure monitor 30. Alternatively or additionally, the dialysis device 12 may be configured to initiate repositioning of the patient, i.e., into the so-called Tendelenburg position, in response to the received warning signal. Alternatively or additionally, the dialysis device 12 may be configured to request medical staff in response to the received warning signal. Alternatively or additionally, the dialysis device 12 may be configured to interrupt an ultrafiltration treatment in response to the received warning signal.

In a further development, the alarm unit 24 may be configured to output a two-level warning signal. In this configuration, the alarm unit 24 may be configured to output a first warning signal when the determined blood pressure value falls below the initial blood pressure value determined or measured at the beginning of the dialysis treatment by a value between 15 and 20 mmHg. Further, the alarm unit 24 may be configured to output a second warning signal when the blood pressure value determined during the dialysis treatment falls at least 20 mmHg below the initial blood pressure value determined or measured at the beginning of the dialysis treatment.

In one configuration, the dialysis device 12 may be configured to, in response to the warning signal, at first, carry out a measurement using the further blood pressure monitor 30. Only if this measurement indicates that the measured blood pressure value has reached the threshold value, an alarm signal, i.e., directed to the medical staff, is output and/or the ultrafiltration treatment is interrupted and/or a change of the patient's position is initiated.

In the further development, the dialysis device 12 may be configured to control an ultrafiltration treatment carried out by the dialysis device 12 on the basis of the blood pressure values determined by means of the blood pressure monitor 14 and transmitted thereto via the interfaces 26, 28. For doing so, the thus transmitted blood pressure values may be used as input values for a closed loop control circuit for controlling an ultrafiltration rate in the ultrafiltration treatment.

It will be obvious for a person skilled in the art that these embodiments and items only depict examples of a plurality of possibilities. Hence, the embodiments shown here should not be understood to form a limitation of these features and configurations. Any possible combination and configuration of the described features can be chosen according to the scope of the invention.

LIST OF REFERENCE NUMERALS

10 Dialysis system
12 Dialysis device
14 Blood pressure monitor
16 Wristband
18 Measuring unit
20 Control unit
22 Memory unit
24 Alarm unit
26 Wireless interface of the blood pressure monitor
28 Wireless interface of the dialysis device
30 Further blood pressure monitor
32 Cuff
34 Further memory unit

The invention claimed is:

1. A method for determining a blood pressure value of a patient, the method comprising:
   determining a pulse course of the patient;
   normalizing the pulse course using a duration of a cardiac cycle as a measure of scale;
   selecting a single reference point in the pulse course, wherein:
      the single reference point is within a transition area from systole to diastole of the cardiac cycle of the patient;
      the single reference point corresponds to a point of inflection in the pulse course; and
      the pulse course has a positive rate of change or slope at the point of inflection;
   providing a mathematical function for determining the blood pressure value as a function of a time corresponding to the single reference point and an amplitude corresponding to the single reference point, wherein the mathematical function correlates a quotient formed by the time corresponding to the single reference point and the amplitude corresponding to the single reference point to the blood pressure value;
   determining the blood pressure value using the mathematical function, wherein the time corresponding to the single reference point and the amplitude corresponding to the single reference point are the only variables inputted to the mathematical function to determine the blood pressure value; and
   outputting a warning signal when the determined blood pressure value has reached a predetermined threshold value.

2. The method according to claim 1, wherein the transition area is disposed between a local minimum and a local maximum of the pulse course.

3. The method according to claim 1, wherein the blood pressure value corresponds to a systolic blood pressure value, a diastolic blood pressure value, or a mean arterial blood pressure value.

4. The method according to claim 1, wherein the pulse course is determined based on time-based and volume-based blood flow values in a tissue section of the patient.

5. The method according to claim 4, wherein the pulse course is determined by photoplethysmography.

6. The method according to claim 1, wherein the pulse course is normalized using a maximum amplitude, as a measure of scale.

7. The method according to claim 1, wherein the single reference point is determined based on a rate of change of the pulse course.

8. The method according to claim 1, wherein the mathematical function is a linear function or polynomial function which correlates, the time corresponding to the single reference point and the amplitude corresponding to the single reference point to the blood pressure.

9. The method according to claim 1, wherein providing the mathematical function comprises:
   providing at least two data sets, each of which comprises a measured blood pressure value and an associated time corresponding to the single reference point and amplitude corresponding to the single reference point; and
   determining the mathematical function on the basis of the provided data sets by an interpolation method or a regression analysis method.

10. The method according to claim 1, wherein the predetermined threshold value is determined with respect to a blood pressure value of a preceding cardiac cycle at a beginning of a medical treatment.

11. The method according to claim 1, wherein the blood pressure value is determined according to the formula:

$$BP_n = c_3 + m_3 \times t_{RP\_n}/h_{RP\_n}$$

wherein $BP_n$ is the blood pressure value associated with the cardiac cycle, c3 is a constant of the mathematical function, $m_3$ is a slope of the mathematical function, $t_{RP\_n}$ is the time corresponding to the single reference point, and $h_{RP\_n}$ is the amplitude corresponding to the single reference point.

12. A blood pressure monitor for determining a blood pressure value of a patient, comprising:
   a measuring unit for determining a pulse course of the patient; and
   a control unit configured to perform one or more operations comprising:
      normalizing the pulse course using a duration of cardiac cycle as a measure of scale;
      selecting a single reference point in the pulse course, wherein:
         the single reference point being within a transition area from systole to diastole of the cardiac cycle of the patient;
         the single reference point corresponds to a point of inflection in the pulse course; and
         the pulse course has a positive rate of change or slope at the point of inflection;
      providing a mathematical function for determining the blood pressure value as a function of a time corresponding to the single reference point and an amplitude corresponding to the single reference point, wherein the mathematical function correlates a quotient formed by the time corresponding to the single reference point and the amplitude corresponding to the single reference point to the blood pressure value;
      determining the blood pressure value using the mathematical function, wherein the time corresponding to the determined single reference point and the amplitude corresponding to the determined single reference point are the only variables inputted to the mathematical function to determine the blood pressure value; and outputting a warning signal when the determined blood pressure value has reached a predetermined threshold value.

13. The blood pressure monitor according to claim 12, further comprising an interface configured for exchanging data, wherein based on the measured blood pressure value, the blood pressure monitor is configured for providing or adjusting the mathematical function by which the blood pressure value is determined based on the determined single reference point.

14. The blood pressure monitor according to claim 12, wherein the predetermined threshold value is determined with respect to a blood pressure value of a preceding cardiac cycle at a beginning of a medical treatment.

15. A dialysis system comprising a blood pressure monitor according to claim 12.

16. The blood pressure monitor according to claim 12, wherein the blood pressure monitor is configured to determine the blood pressure value according to the formula:

$$BP_n = c_3 + m_3 \times t_{RP\_n} / h_{RP\_n}$$

wherein $BP_n$ is the blood pressure value associated with the cardiac cycle, c3 is a constant of the mathematical function, $m_3$ is a slope of the mathematical function, $t_{RP\_n}$ is the time corresponding to the single reference point, and $h_{RP\_n}$ is the amplitude corresponding to the single reference point.

* * * * *

UNITED STATES PATENT AND TRADEMARK OFFICE
CERTIFICATE OF CORRECTION

| | | |
|---|---|---|
| PATENT NO. | : 12,290,341 B2 | Page 1 of 1 |
| APPLICATION NO. | : 17/426417 | |
| DATED | : May 6, 2025 | |
| INVENTOR(S) | : Zhang Wei and Christof Rüth | |

It is certified that error appears in the above-identified patent and that said Letters Patent is hereby corrected as shown below:

In the Specification

Column 1, Line 12, delete "10 10 2019 102 178.2," and insert --10 2019 102 178.2,--.

In the Claims

Claim 8
Column 16, Line 9, delete "correlates," and insert --correlates--.
Column 16, Line 11, delete "pressure" and insert --pressure value--.

Claim 11
Column 16, Line 30, delete "c3" and insert --$c_3$--.

Claim 16
Column 17, Line 23, delete "c3" and insert --$c_3$--.

Signed and Sealed this
Seventeenth Day of June, 2025

Coke Morgan Stewart
*Acting Director of the United States Patent and Trademark Office*